(12) United States Patent
Charlebois et al.

(10) Patent No.: US 10,265,200 B2
(45) Date of Patent: Apr. 23, 2019

(54) MEDICAL PROSTHESES HAVING BUNDLED AND NON-BUNDLED REGIONS

(75) Inventors: Steven J. Charlebois, West Lafayette, IN (US); William Kurt Dierking, Louisville, KY (US); Matthew S. Huser, West Lafayette, IN (US); Keith Milner, West Lafayette, IN (US); Jichao Sun, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 115 days.

(21) Appl. No.: 13/814,179

(22) PCT Filed: Aug. 10, 2010

(86) PCT No.: PCT/US2010/044984
§ 371 (c)(1),
(2), (4) Date: May 6, 2013

(87) PCT Pub. No.: WO2012/021125
PCT Pub. Date: Feb. 16, 2012

(65) Prior Publication Data
US 2013/0211497 A1    Aug. 15, 2013

(51) Int. Cl.
*A61F 2/82* (2013.01)
*A61F 2/07* (2013.01)
*A61F 2/89* (2013.01)

(52) U.S. Cl.
CPC ............... *A61F 2/82* (2013.01); *A61F 2/07* (2013.01); *A61F 2/89* (2013.01);
(Continued)

(58) Field of Classification Search
CPC .. A61F 2/0063; A61F 2002/068; A61F 2/007; A61F 2/01; A61F 2002/016;
(Continued)

(56) References Cited

U.S. PATENT DOCUMENTS 5,116,360 A    5/1992 Pinchuk et al.
5,123,917 A    6/1992 Lee
(Continued)

FOREIGN PATENT DOCUMENTS

WO    WO2001/26562    4/2001

OTHER PUBLICATIONS

International search report and written opinion for PCT/US2010/044984 dated Oct. 7, 2010, 15 pgs.
(Continued)

*Primary Examiner* — Leslie Lopez
(74) *Attorney, Agent, or Firm* — Brinks Gilson & Lione (57) ABSTRACT

The present embodiments provide an endoluminal prosthesis, such as a stent-graft, having a relatively low delivery profile. In one embodiment, the prosthesis comprises a membrane, and at least one stent having contracted and expanded states, where the stent is coupled to the membrane and maintains patency in the expanded state. The prosthesis further may comprise selectively oriented axial and/or circumferential fibers arranged at predetermined locations along the length and circumference of the prosthesis. An increased population density of the circumferential and/or axial fibers may be provided in areas in which the at least one stent portion is attached to the membrane, or in areas of higher physiological loads imposed upon the endoluminal prosthesis. Selectively orienting axial fibers and circumferential fibers at predetermined locations along the length and circumference of the prosthesis, but not continuously along the entire prosthesis, significantly reduces delivery profile due to the reduction in graft material.

17 Claims, 5 Drawing Sheets

(52) U.S. Cl.
CPC . *A61F 2002/075* (2013.01); *A61F 2250/0017* (2013.01); *A61F 2250/0028* (2013.01)

(58) Field of Classification Search
CPC ........ A61F 2002/018; A61F 2/02; A61F 2/04; A61F 2/06; A61F 2/07; A61F 2002/072; A61F 2002/075; A61F 2/82; A61F 2/86; A61F 2/90; A61F 2250/0017; A61F 2250/0028
USPC .................... 623/1.13, 1.15, 1.16, 1.32–1.33
See application file for complete search history.

(56) References Cited

U.S. PATENT DOCUMENTS

| | | | |
|---|---|---|---|
| 5,667,523 | A | 9/1997 | Bynon et al. |
| 5,676,670 | A | 10/1997 | Kim |
| 5,676,671 | A * | 10/1997 | Inoue ........................ A61F 2/95 604/247 |
| 5,735,892 | A * | 4/1998 | Myers ........................ A61F 2/07 606/198 |
| 5,925,074 | A | 7/1999 | Gingras et al. |
| 6,287,335 | B1 * | 9/2001 | Drasler et al. ............... 623/1.28 |
| 6,514,282 | B1 * | 2/2003 | Inoue ........................ A61F 2/95 623/1.13 |
| 6,709,455 | B1 | 3/2004 | Chouinard |
| 6,939,377 | B2 | 9/2005 | Jayaraman et al. |
| 2002/0052660 | A1 * | 5/2002 | Greenhalgh .......... A61F 2/0063 623/23.7 |
| 2005/0070992 | A1 * | 3/2005 | Bolduc et al. ............... 623/1.15 |
| 2006/0034769 | A1 * | 2/2006 | Kohn ...................... A61L 31/06 424/9.45 |
| 2006/0212113 | A1 | 9/2006 | Shaolian et al. |
| 2008/0175980 | A1 * | 7/2008 | Sun ........................ B05D 1/002 427/2.25 |
| 2009/0163951 | A1 | 6/2009 | Simmons et al. |
| 2009/0187240 | A1 | 7/2009 | Clerc et al. |
| 2010/0191319 | A1 * | 7/2010 | Lilburn et al. ............... 623/1.15 |

OTHER PUBLICATIONS

Murray et al, "Vascular Graft Healing. III. FTIR Analysis of ePTFE Graft Samples From Implanted Bigrafts", J. Biomed Mater Res B Appl Biomater, Aug. 15, 2004; 70(2), Abstract, 1 pg.
International Preliminary Report on Patentability for PCT/US2010/044984 dated Feb. 21, 2013, 12 pgs.
Supplemental European Search Report for European Patent Application No. 10855978.2 dated Feb. 25, 2014, 8 pgs.
Response to Office Action for European Patent Application No. 10855978.2 dated Sep. 4, 2014, 6 pgs.
Decision to Grant EP10855978.2 dated Oct. 16, 2015, 31 pgs.
Extended European Search Report for Ep 16156978.5 dated Jun. 1, 2016, 8 pgs.

* cited by examiner

MEDICAL PROSTHESES HAVING BUNDLED AND NON-BUNDLED REGIONS

RELATED APPLICATIONS

The present patent document is a § 371 filing based on PCT Application Serial No. PCT/US2010/0044984, filed Aug. 10, 2010 (and published as WO 2012/021125A1 on Feb. 16, 2012), designating the United States and published in English, which is hereby incorporated by reference in its entirety.

BACKGROUND

Apparatus and methods for treating vascular conditions, and more specifically, materials for use in treating such conditions, are described.

Stent-graft assemblies may be used to treat a number of medical conditions. One common use of stent-graft assemblies relates to the treatment of an aneurysm, which is an abnormal widening or ballooning of a portion of an artery that may be caused by a weakness in the blood vessel wall. In many cases, the internal bleeding is so massive that a patient can die within minutes of an aneurysm rupture. For example, in the case of aortic aneurysms, the survival rate after a rupture may be as low as 20%.

In an endovascular treatment of a blood vessel using a stent-graft, the stent-graft is positioned in the blood vessel across the aneurysm, e.g., using catheter-based placement techniques. The stent-graft treats the aneurysm by sealing the wall of the blood vessel with a generally impermeable graft material. Thus, the aneurysm is sealed off and blood flow is kept within the primary passageway of the blood vessel. Although stent-grafts are frequently used for treating aneurysms, other medical treatments also use stent-grafts and still other uses are possible, such as uses for treating aortic dissections, stenosed arteries or other conditions.

Various types of stent-grafts are constructed with a stent disposed inside graft material, outside of graft material, or between inner and outer layers of graft material. The stents commonly are coupled to the one or more layers of graft material. For example, one technique for securing graft material to a stent involves securing one or more graft layers to the struts of the stent.

Another technique that is used for securing graft layers to a stent generally involves encapsulating the stent or a portion thereof with an inner and an outer layer of graft material. In this type of stent-graft, the two layers of graft material are adhered to each other through open areas in the stent structure. Some additional bonding may also occur between each graft layer and the stent structure itself, for example, the inner and outer graft layers may be adhered by heating or using adhesives.

In constructing stent-grafts, it may be difficult to furnish a reliable prosthesis having a relatively small diameter delivery profile, such that the prosthesis may be delivered into smaller vessels. Notably, the inventors have determined that the fabric portion of a stent-graft can contribute significantly to the overall delivery profile of a stent-graft. For example, graft material, depending on its thickness, may contribute between about 50-80% of the overall volume of a stent-graft's profile in a delivery configuration. Thus, such relatively large prostheses may not be capable of delivery into smaller vessels. However, the fabric used in stent-grafts for endovascular graft repair must maintain important and unique requirements, including sufficient tensile strength, permeability, biocompatibility, and overall bulk, and such properties should not be compromised in order to achieve the desired smaller profile.

SUMMARY

The present embodiments provide an endoluminal prosthesis having beneficial properties and a relatively low delivery profile.

In a first embodiment, the prosthesis comprises a membrane having a lumen for carrying fluid flow, and further comprises a plurality of circumferential fibers coupled to the membrane. The plurality of circumferential fibers form at least one bundled region in which at least two adjacent circumferential fibers are separated by a first spacing, and form at least one non-bundled region in which at least two adjacent circumferential fibers are separated by a second spacing, where the first spacing is less than the second spacing. In one example, the second spacing in the non-bundled region is at least three times greater than the first spacing in the bundled region.

In one embodiment, at least one stent is coupled to the membrane in at least one bundled region of the stent. By way of example, where the stent comprises a zig-zag shape having proximal and distal apices, at least one of the proximal apices of the stent is secured to the membrane at a proximal bundled region, and at least one of the distal apices of the stent is secured to the membrane at a distal bundled region. The proximal and distal bundled regions may be separated by at least one non-bundled region.

A plurality of axial fibers also may be provided that extend in a direction that is generally parallel to a longitudinal axis of the endoluminal prosthesis. The plurality of axial fibers may overlap with at least one bundled region of circumferential fibers at intersections, and at least one portion of the stent may be secured to the membrane at one of the intersections. Optionally, a plurality of angled axial fibers also may be selectively provided.

Advantageously, by selectively orienting circumferential fibers and/or axial fibers at predetermined locations along the length and circumference of the prosthesis, a specifically reinforced prosthesis may be provided. For example, an increased population density of the circumferential fibers and/or the axial fibers may be provided in areas in which the at least one stent portion is attached to the membrane. As another example, an increased population density of the circumferential and/or axial fibers may be provided in areas of higher physiological loads imposed upon the endoluminal prosthesis. Thus, by selectively orienting axial fibers and circumferential fibers at predetermined locations along the length and circumference of the prosthesis, but not continuously along the entire graft, a significantly reduced delivery profile may be achieved due to the reduction in graft material. However, strength and integrity characteristics of the stent-graft are maintained.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
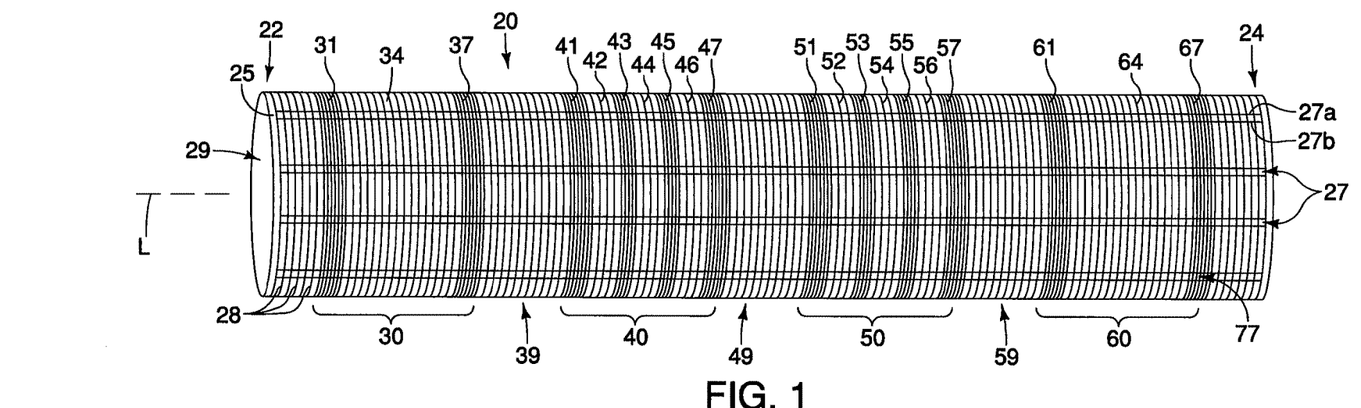
FIG. 1 is side view of a stent-graft according to a first embodiment with stents removed for illustrative purposes.
Figure 2:
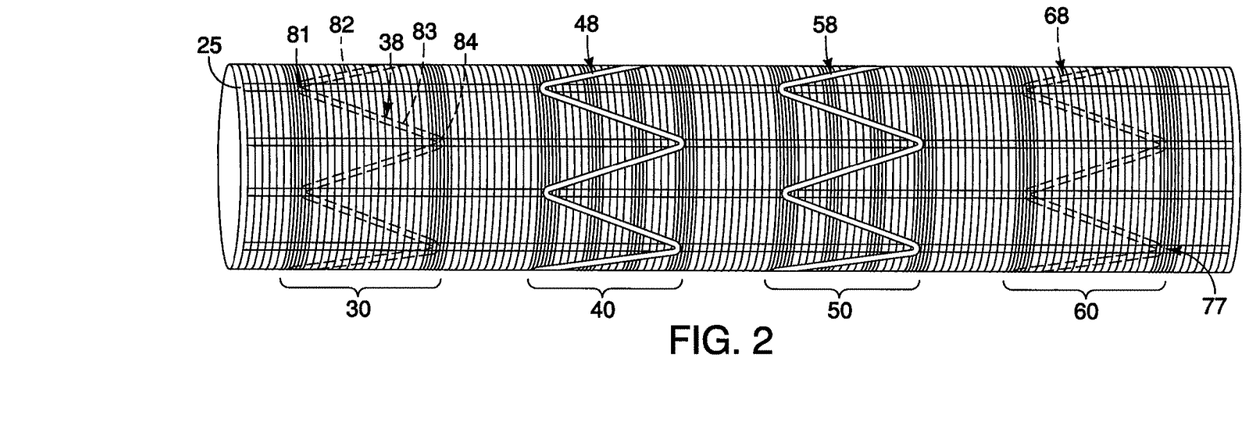
FIG. 2 is side view of the stent-graft of FIG. 1 with stents shown.

Referring now to FIGS. 1-2, a first embodiment of a stent-graft 20 is shown. As shown in FIG. 1, the stent-graft 20 comprises a membrane 25 having proximal and distal ends 22 and 24, respectively, and a lumen 29 extending therebetween that is dimensioned for fluid flow for a given application.

The stent-graft 20 further comprises at least one axial fiber 27 and at least one circumferential fiber 28. Preferably, a plurality of axial fibers 27 and circumferential fibers 28 are provided, and are arranged in predetermined patterns for one or more desired functions, such as providing stent attachment locations and/or being positioned in regions along the stent-graft 20 that are subject to relatively high hydrodynamic forces, as explained further below. For example, the axial fibers 27 may assist in withstanding longitudinally-oriented blood flow forces, while the circumferential fibers 28 may assist in withstanding pulsatile flow forces.

Advantageously, by selectively orienting the axial fibers 27 and circumferential fibers 28 at predetermined locations along the length and circumference of the stent-graft 20, but not continuously along the entire stent-graft, a significantly reduced delivery profile may be achieved due to the reduction in fiber material.

In the exemplary embodiment of FIGS. 1-2, the stent-graft 20 comprises a plurality of distinct regions, each for accommodating a stent or portion of a stent. By way of example, four distinct regions 30, 40, 50 and 60 are provided for accommodating stents 38, 48, 58 and 68, respectively. Each of the four distinct regions 30, 40, 50 and 60 comprises a predetermined arrangement of axial fibers 27 and circumferential fibers 28 for accommodating the respective stents 38, 48, 58 and 68.

For example, the first distinct region 30 may be disposed near the proximal end 22 of the prosthesis. As shown in FIG. 1, the first distinct region 30 comprises a plurality of circumferential fibers 28 arranged in predetermined orientations. In particular, a proximal bundled region 31 of the first distinct region 30 comprises multiple circumferential fibers 28 coupled to the membrane 25. The circumferential fibers 28 are arranged such that at least two adjacent circumferential fibers 28 within the proximal bundle 31 are separated by a first spacing.

The first distinct region 30 further comprises a distal bundled region 37 that, like the proximal bundled region 31, comprises at least two adjacent circumferential fibers 28 separated by the same first spacing as the proximal bundled region 31. The proximal and distal bundled regions 31 and 37 may comprise a desired number of circumferential threads per inch ("TPI").

The first distinct region 30 further comprises at least one non-bundled region 34, which is disposed between the proximal and distal bundled regions 31 and 37. The non-bundled region 34 comprises at least two adjacent circumferential fibers 28 that are separated by a second spacing, which is greater than the first spacing. In other words, as depicted in FIGS. 1-2, at least some, if not all, of the circumferential fibers 28 of the non-bundled region 34 are separated by a greater spacing as compared to the circumferential fibers 28 of the proximal and distal bundled regions 31 and 37. Notably, in one embodiment, the first spacing may be zero, i.e., there is no separation of fibers.

In the example of FIGS. 1-2, the proximal and distal bundles 31 and 37 may have a greater TPI count of circumferential fibers 28 relative to the non-bundled region 34. Solely by way of example, and without limitation, the proximal and distal bundled regions 31 and 37 may have a thread count between about 20 to about 120 TPI. In contrast, the non-bundled region 34 may have a thread count of less than 20 TPI. Therefore, in this example, there is a non-uniform circumferential fiber population density along at least a portion of the stent-graft 20. Additionally, the number of fibers in each of the bundled and non-bundled regions may also vary. For example, one bundled region may have more fibers than another bundled region, and similarly for the non-bundled regions.

In one example, the first spacing within the proximal and distal bundled regions 31 and 37 may be such that the spacing between individual circumferential fibers 28 is less than or equal to the width of the fibers themselves. Thus, adjacent circumferential fibers may abut one another directly, or may be separated but disposed in such close proximity such that another fiber of the same width cannot be disposed therebetween without overlap. By contrast, circumferential fibers 28 disposed in the non-bundled region 34 are not in direct proximity to one another, such that the second spacing between individual circumferential fibers 28 is greater than the width of the fibers themselves. The spacing between the fibers in each of the bundled regions need not be identical. Similarly, the spacing of the fibers in the non-bundled regions need not be identical.

The stents 38, 48, 58 and 68 may comprise any suitable shape for providing desired support to the stent-graft 20. In one non-limiting example, shown herein, the stents may comprise a generally zig-zag shape formed from a single wire comprising a plurality of substantially straight first segments 82 and second segments 83 having bent segments disposed therebetween, the bent segments in the form of proximal apices 81 and distal apices 84. In one embodiment, each of the proximal apices 81 of the first stent 38 is positioned to overlap with the proximal bundled region 31, and each of the distal apices 84 of the first stent 38 is positioned to overlap with the distal bundled region 37, as shown in FIG. 2. While z-stents are depicted herein, the embodiments are not limited to z-stents and other stent structures may be used.

Advantageously, by selectively overlapping the proximal apices 81 of the first stent 38 with the proximal bundled region 31, an enhanced suture attachment site may be provided due to the close proximity of the circumferential sutures 28 within the proximal bundle 31. For example, it may be easier to suture the proximal apices 81 of the stent 38 to the stent-graft 20 in areas where circumferential fibers are bundled, instead of relatively spaced apart or lacking entirely. Similarly, by selectively overlapping the distal apices 84 of the first stent 38 with the distal bundled region 37, an enhanced suture attachment site may be provided due within the distal bundled region 37.

Moreover, in the example of FIGS. 1-2, at least two axial fibers 27a and 27b preferably overlap with the various circumferential fiber bundles at intersections 77. Each of the proximal and distal apices 81 and 84 of the stent 38 may be aligned with one of the intersections 77, as shown in FIG. 2. Thus, each of the proximal and distal apices 81 and 84 of the stent 38 may be secured to the stent-graft 20 in regions where a circumferential fiber bundled region meets axial fibers 27, thereby providing selective suture attachment zones for the stent 38. Notably in this example, there is a selective axial fiber density along at least a portion of the stent-graft 20, since axial fibers 27 are intended to only line up with the proximal and distal apices of a given stent and the fibers.

As a further advantage, by selectively orienting axial fibers 27 and circumferential fibers 28 at predetermined locations along the length and circumference of the stent-graft 20, e.g., at specific points of attachment of proximal and distal stent apices, but not continuously along the entire stent-graft 20, a significantly reduced delivery profile may be achieved due to the reduced presence of fiber material.

Referring still to FIGS. 1-2, in this embodiment the other stents 48, 58 and 68 may be attached to the stent-graft 20 in a similar manner. In particular, the stent 48 may be positioned to overlap with the second distinct region 40. The second distinct region 40 may comprise a proximal bundled region 41, intermediate bundled regions 43 and 45, and a distal bundled region 47, each comprising at least some circumferential fibers 28 disposed with the first spacing relative to one another, as shown in FIG. 1. Non-bundled regions 42, 44 and 46 may be disposed between the various bundled regions 41, 43, 45 and 47, as shown in FIG. 1. Like the stent 30, each of the proximal and distal apices 81 and 84 of the stent 48 may be secured to the stent-graft 20 at intersections 77 where a circumferential fiber bundle meets axial fibers 27. Specifically, the proximal apices 81 of the stent 48 are attached to the stent-graft 20 where proximal bundled region 41 meets axial fibers 27, while the distal apices 84 of the stent 48 are attached to the stent-graft 20 where distal bundled region 47 meets axial fibers 27. Further, the stent 48 may be secured to the stent-graft 20 at locations in which the substantially straight first segments 82 and second segments 83 of the stent 48 overlap with the intermediate bundles 43 and 45. In this manner, multiple specific suture attachment zones are provided for the stent 48 at the bundled regions 41, 43, 45 and 47, while the provision of non-bundled regions 42, 44 and 46 may contribute to reducing the overall profile of the stent-graft 20 while preferably comprising some circumferential fibers for distributing loads.

Stent 58 may be positioned to overlap with the third distinct region 50 in a similar manner that stent 48 is positioned relative to the second distinct region 40. Specifically, the third distinct region 50 may comprise a proximal bundled region 51, intermediate bundled regions 53 and 55, and a distal bundled region 57, while non-bundled regions 52, 54 and 56 are disposed between the various bundles regions 51, 53, 55 and 57. Like the stents 30 and 40, each of the proximal and distal apices 81 and 84 of the stent 58 may be secured to the stent-graft 20 at intersections 77 where a circumferential fiber bundle meets axial fibers 27.

Finally, stent 68 may be positioned to overlap with the fourth distinct region 60 in a similar manner that stent 38 is positioned relative to the first distinct region 30. Specifically, the fourth distinct region 60 comprise proximal and distal bundled regions 61 and 67, with non-bundled region 64 disposed therebetween. Like the stent 30, each of the proximal and distal apices 81 and 84 of the stent 68 may be secured to the stent-graft 20 at intersections 77 where a circumferential fiber bundle meets axial fibers 27.

Notably, non-bundled spacing regions 39, 49 and 59 are positioned between the distinct regions 30, 40, 50 and 60, as shown in FIGS. 1-2. Circumferential fibers of the non-bundled spacing regions 39, 49 and 59 may comprise the second spacing relative to one another, i.e., a greater spacing than in the bundled regions. Thus, there is a reduction in fiber material in the non-bundled spacing regions 39, 49 and 59, contributing to a reduced delivery profile.

Beneficially, a fiber-reinforced polymer matrix may be provided that is designed to carry the necessary supporting stents, plus withstand known loading conditions during long term use in a particular application, such as in endovascular use.

While intermediate bundled regions are shown only for the second and third distinct regions 40 and 50, it will be apparent that any of the various distinct regions 30, 40, 50 and 60 may comprise one or more intermediate bundled regions, or the various distinct regions each may omit intermediate bundled regions. Moreover, the exact placement of the bundled and non-bundled regions may be varied, e.g., based on desired stent attachment sites, hydrodynamic forces expected to be imposed upon on the stent-graft 20, and other factors.

The membrane 25 may be disposed internal or external to the axial fibers 27 and circumferential fibers 28. In the example of FIGS. 1-2, the membrane 25 is disposed internal to both the axial and circumferential fibers 27 and 28, but this is not required. In this instance, the membrane 25 may be formed upon a mandrel, with the desired circumferential and axial fiber pattern being deposited externally thereof.

Further, the stents 38, 48, 58 and 68 may be positioned external and/or internal relative to the membrane 25, as well as external and/or internal relative to the axial fibers 27 and circumferential fibers 28. In the example of FIGS. 1-2, the stents 38 and 68 are disposed internal (dashed lines) relative to the membrane 25, while the stents 48 and 58 are disposed external of both the membrane 25 and the axial and circumferential fibers 27 and 28. However, various combinations of internal and external positioning of the membrane, stents and fibers are possible. Moreover, lamination and/or embedding of the stents between two membranes may be provided in lieu of suturing the stents. In the latter embodiment, selective fiber densities still may be provided for the purpose of providing reinforcement areas for expected physiological forces.

During manufacture, the materials may be placed on a mandrel in a desired orientation. In one exemplary manufacturing step, the stent-graft 20 may be prepared by mounting the membrane 25 on a mandrel and then overlaying the axial fibers 27 and circumferential fibers 28 in a desired orientation. Alternatively, the axial fibers 27 and circumferential fibers 28 may be arranged on the mandrel in a desired orientation, then the membrane 25 may be disposed over the fibers. In one other embodiment, the axial fibers 27 and circumferential fibers 28 may be arranged on the mandrel in a desired orientation, then the stents 38, 48, 58 and 68 may be laid over the fibers, and then the membrane 25 may be disposed over the fibers and the stents. As a further alternative, one membrane may be placed on the mandrel, then the axial fibers 27 and circumferential fibers 28 may be deposited onto the first mandrel, and then a second membrane may be deposited over the first membrane and the axial and circumferential fibers 27 and 28. Still further, only some fibers may be applied to the mandrel, such as the circumferential fibers 28, then the membrane 25 may be deposited thereon, and then other fibers, such as the axial fibers 27, may be deposited over the circumferential fibers 28 and the membrane 25. In sum, various assembly combinations are possible.

Various mechanisms may be used to correctly deposit and align the axial fibers 27 and circumferential fibers 28 in the desired orientation, such as automated CNC deposition. The membrane 25 with axial and circumferential fibers 27 and 28 then may be mounted on a lathe. The lathe may be rotated at a proper speed, such as 20 rpm, while applying a dilute polyurethane solution to cover all of the fibers. The stent-graft 20 then may be cured or dried at about 65 degrees Celsius for about 2 hours while the lathe is rotated at the desired speed.

The stents then may be secured to the membrane 25, preferably near one or more intersections 77, as explained above. In one example, the mandrel used to assemble the materials may comprise pins at predetermined locations. Various fibers may be arranged around the pins, such that when the assembled device is removed from the mandrel, the pins have created bores. The bores created by the mandrel pins may advantageously provide a predetermined suture attachment site for subsequent attachment of the stents to the membrane.

Optionally, the stents may be coupled to the membrane 25 using polymer encapsulation as the adhesion technique, thereby eliminating the need for sutures. Regardless of the technique used to couple the stents to the membrane 25, by selectively orienting axial fibers 27 and circumferential fibers 28 at predetermined locations along the length and circumference of the stent-graft 20, but not continuously along the entire stent-graft 20, a significantly reduced delivery profile may be achieved.

In one embodiment, the membrane 25 may comprise a polymeric sheet having a suitable porosity, depending on the application. In one example, a polymeric sheet may comprise the polyurethane Thoralon®. As described in U.S. Pat. No. 6,939,377, incorporated herein by reference in its entirety, Thoralon® is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (Thoratec® Corporation, Pleasanton, Calif.) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

The SMA-300 component (Thoratec® Corporation, Pleasanton, Calif.) is a polyurethane comprising polydimethylsiloxane as a soft segment and the reaction product of MDI and 1,4-butanediol as a hard segment. A porous polymeric sheet can be formed from these two components by dissolving the base polymer and additive in a solvent such as dimethylacetamide (DMAC) and solidifying the mixture by solvent casting or by coagulation in a liquid that is a non-solvent for the base polymer and additive.

Thoralon® has been used in certain vascular applications and is characterized by thromboresistance, high tensile strength, low water absorption, low critical surface tension, and good flex life. Thoralon® is believed to be biostable and to be useful in vivo in long term blood contacting applications requiring biostability and leak resistance. Because of its flexibility, Thoralon® may be useful in larger vessels, such as the abdominal aorta, where elasticity and compliance are beneficial.

Further, Thoralon® may also be used as a drug delivery vehicle, for example, to deliver one or more therapeutic agents. The therapeutic agents may be coated onto or contained within a porous outer layer of the membrane 25 for sustained release subsequent to an implantation procedure and may be used, for example, to promote intimal cell in-growth.

While Thoralon® is one example, the membrane 25 may comprise other materials. In addition to, or in lieu of, a polyurethane such as Thoralon®, the membrane 25 may comprise any biocompatible polymeric material including non-porous or substantially non-porous polyurethanes, PTFE, expanded PTFE (ePTFE), polyethylene tetraphthalate (PET), aliphatic polyoxaesters, polylactides, polycaprolactones, hydrogels, and other non-polymeric materials.

The stent-graft 20 may be used in a wide range of procedures, for example, to treat an aneurysm, stenosis, dissection or other condition. As known in the art, stents 38, 48, 58 and 68 have compressed, reduced diameter delivery states in which the stent-graft 20 may be advanced to a target location within a vessel, duct or other anatomical site, and further have expanded states, as shown in FIG. 2, in which they may be configured to apply a radially outward force upon the vessel, duct or other target location, e.g., to maintain patency within a passageway, while the lumen 29 is suitable for carrying fluid though the stent-graft 20. The stent-graft 20 may be designed specifically for treating abdominal or thoracic aneurysms or dissections. Moreover, while a single lumen device is shown, the principles used herein may be used in connection with bifurcated stent-grafts.

The stents 38, 48, 58 and 68 may be made from numerous metals and alloys. In one example, the stents 38, 48, 58 and 68 comprise a shape-memory material such as a nickel-titanium alloy ("nitinol"). Moreover, while generally zig-zag shaped stents are shown, the structure of the stents 38, 48, 58 and 68 may be formed in a variety of ways to provide a suitable intraluminal support structure. For example, one or more stents 30 may be made from a woven wire structure, a laser-cut cannula, individual interconnected rings, or another pattern or design. Depending on the stent structure employed, the position of the fiber bundles may be varied to provide appropriate suture attachment sites in a manner similar to the zig-zag stent example of FIGS. 1-2.

Figure 3:
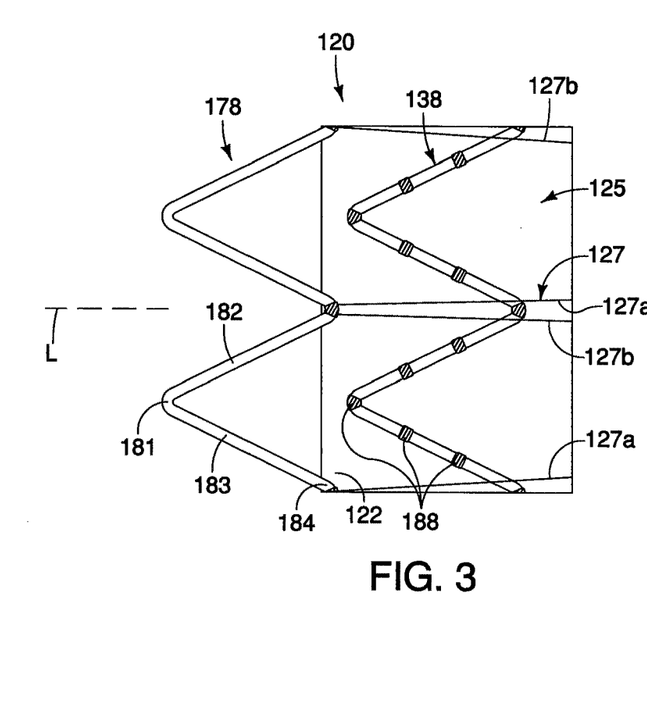
FIG. 3 is a side view of a proximal portion of a stent-graft provided in accordance with an alternative embodiment.

Referring now to FIGS. 3-8, various alternative arrangements of components, in accordance with principles above, are shown and described. For example, in FIG. 3, an alternative stent-graft 120 comprises a membrane 125, stents 138 and 178, and a plurality of angled axial fibers 127. The membrane 125 is similar to the membrane 25 of FIGS. 1-2, and the stents 138 and 178 are similar to the stent 38 of FIGS. 1-2. In this example, the stent 178 is affixed to the proximal end 122 of the membrane 125 and has first and second substantially straight segments 182 and 183 separated by proximal and distal apices 181 and 184. Each of the distal apices 184 may be connected to the proximal end 122 of the membrane 125, as shown in FIG. 3. Furthermore, the stent 138 is coupled to the membrane 125 using a plurality of sutures 188 or other attachment methods as discussed. A plurality of circumferential fiber bundled regions 131, 133, 135 and 137, shown in FIG. 4, may be used in the embodiment of FIG. 3 to provide attachment zones for the sutures 188 to the membrane 125 in the manner noted above in FIGS. 1-2.

In this example, each of the angled axial fibers 127 are disposed around one of the distal apices 184 of the stent 178. The angled axial fibers 127 therefore each form first and second segments 127a and 127b that extend in a distal direction away from the stent 178. The first and second segments 127a and 127b of the angled axial fibers 127 may extend at an angle relative to a longitudinal axis L of the stent-graft. For example, the angle may range from about 1 to about 15 degrees, as depicted in FIG. 3. Notably, such angled axial fibers segments 127a and 127b may be more compliant than the axial and circumferential fibers 27 and 28 shown above, thereby selectively providing compliant support at predetermined locations.

Figure 4:
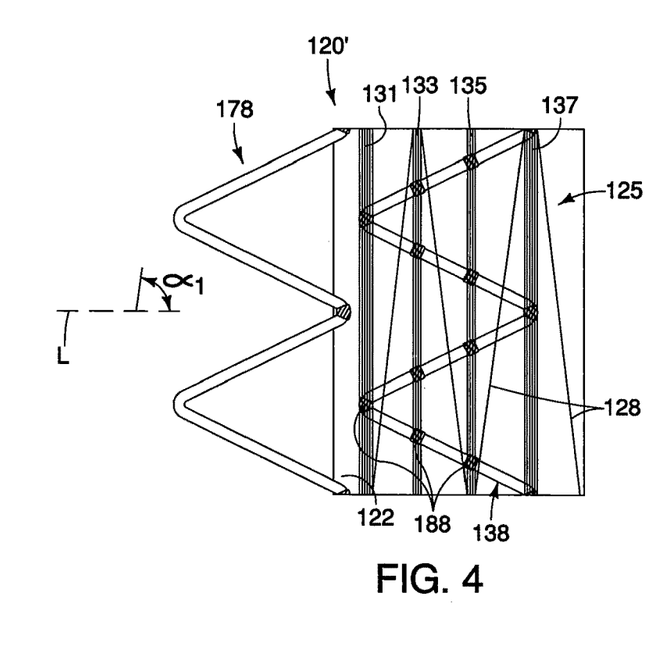
FIG. 4 is a side view of a proximal portion of a stent-graft provided in accordance with a further alternative embodiment.

Referring now to FIG. 4, an exemplary alternative stent-graft 120' is similar to stent-graft 120, and comprises a membrane 125 and stents 138 and 178. A plurality of axial fibers, such as angled axial fibers 127 of FIG. 3, may be employed but are omitted in the illustration. In this example, a plurality of circumferential fibers 128 is provided. Unlike the circumferential sutures 28 of FIGS. 1-2, which are generally perpendicular to the longitudinal axis L of the stent-graft, the circumferential fibers 128 are disposed at angle $\alpha_1$ relative to the longitudinal axis L of the stent-graft, as shown in FIG. 4. In one example, the angle $\alpha_1$ may range from about 70 to about 89 degrees. Like the angled axial fibers segments 127a and 127b of FIG. 3, the angled circumferential fibers 128 of FIG. 4 may be more compliant than the circumferential fibers 28, thereby selectively providing compliant support at predetermined locations.

Figure 5:
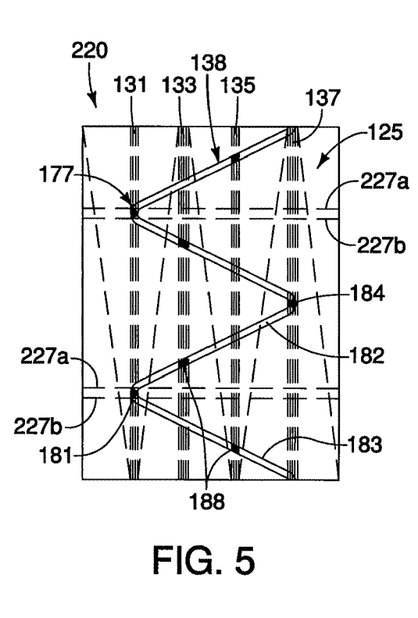
FIGS. 5-7 are side views of portions of various stent-grafts provided in accordance with further alternative embodiments.
Figure 6:
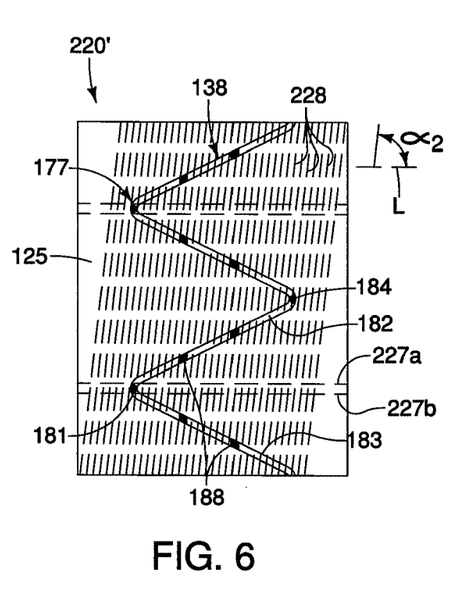
Figure 7:
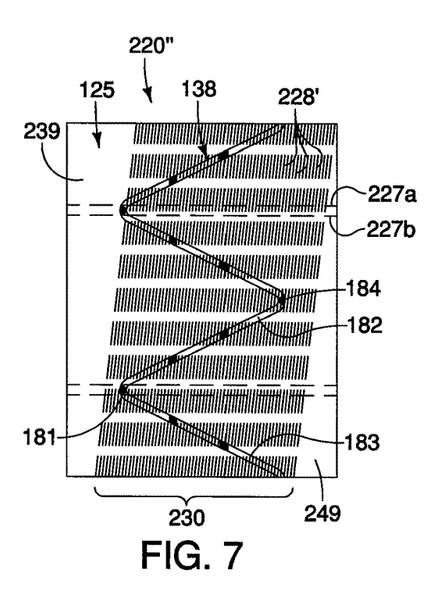

Referring now to FIGS. 5-7, various alternative stent-grafts are shown. Notably, in FIGS. 5-7, various circumferential, axial and angled fibers are depicted with dashed lines for illustrative purposes only, but it is preferred that such circumferential, axial and angled fibers are generally formed from continuous filaments. In FIG. 5, an alternative stent-graft is similar to stent-graft 120, with like reference numerals labeled accordingly. In FIG. 5, at least two axial fibers 227a and 227b preferably overlap with the various circumferential fiber bundled regions 131, 133, 135 and 137 at intersections 177. Each of the proximal apices 181 of the stent 138 may be aligned with one of the intersections 177, as shown in FIG. 5. Thus, each of the proximal apices 181 of the stent 138 may be secured to the stent-graft 220 in regions where a circumferential fiber bundle meets axial fibers 227a and 227b, thereby permitting a significantly enhanced suture attachment zone for at least the proximal apices 181 of the stent 38. Optionally, additional axial fibers may be provided that coincide with the distal apices 184 in a similar manner.

Referring now to FIG. 6, an alternative stent-graft 220' is similar to the stent-graft 220 of FIG. 5. However, in FIG. 6, the plurality of circumferential bundled regions 131, 133, 135 and 137 are omitted, and a plurality of angled circumferential fibers 228 are utilized. The angled circumferential fibers 228 are parallel to one another, but are disposed at an angle $\alpha_2$ relative to the longitudinal axis L of the stent-graft 220'. In one example, the angle $\alpha_2$ is between about 70 to about 89 degrees. Moreover, in this example, the angled circumferential fibers 228 may be wound at between about 10 to about 30 threads per inch (TPI). In FIG. 6, sutures 188 may be coupled to the membrane 125 along multiple parts of each segment 182 and 183 of the stent 138, as well as at each of the proximal and distal apices 181 and 184.

Referring now to FIG. 7, an alternative stent-graft 220" is substantially identical to the stent-graft 220' of FIG. 6. However, in FIG. 7, angled circumferential fibers 228' may be wound at between about 30 to about 50 threads per inch (TPI). Therefore, the closer bundling of angled circumferential fibers 228" in FIG. 7 may provide an enhanced site for attaching sutures 188 to the membrane 125.

Notably, in FIGS. 6-7, the angled circumferential fibers 228 are bundled together along a distinct region 230, which generally overlaps with the stent 138. Non-bundled regions 239 and 249 may exist proximal and distal to the distinct region 230, i.e., in regions where a stent is not present.

Figure 8:
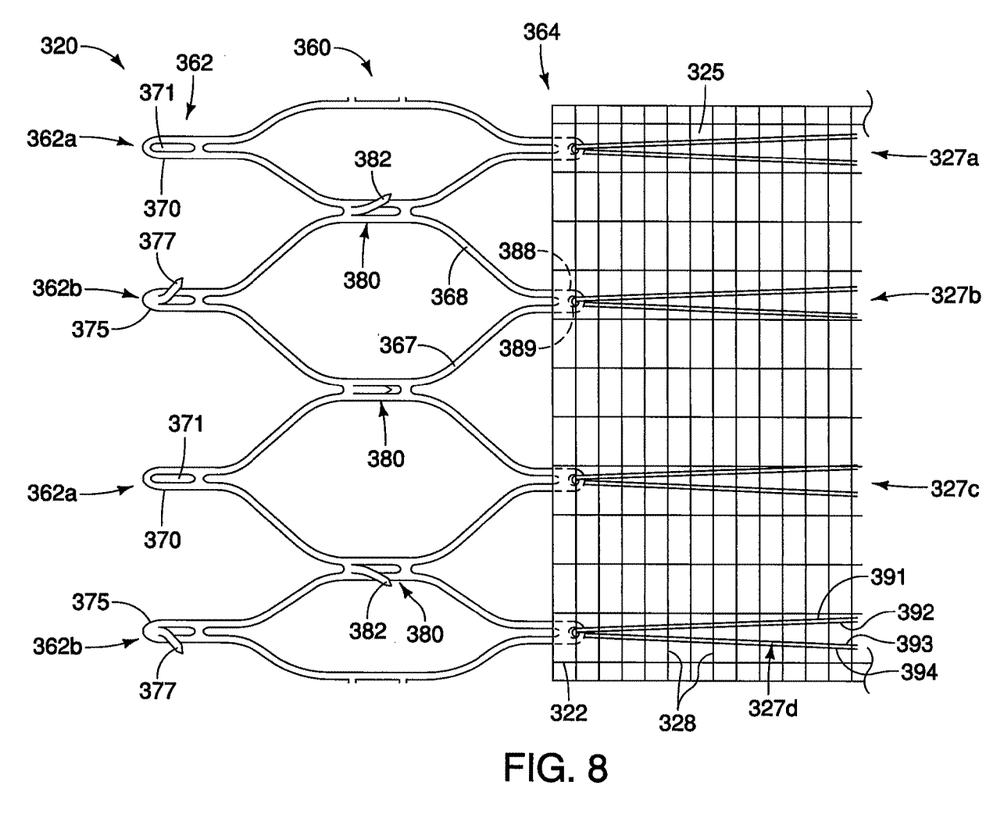
FIG. 8 is a side view of a proximal portion of a stent-graft provided in accordance with a further alternative embodiment.

Referring now to FIG. 8, a proximal portion of an alternative stent-graft 320 is shown and described. In this example, the stent-graft 320 comprises a bare proximal stent 360 that is coupled to a membrane 325. The stent 360 may be manufactured from a continuous cylinder into which a pattern may be cut by a laser or by chemical etching to produce slits in the wall of the cylinder. The resulting structure may then be heat set to give it a desired final configuration. As shown in FIG. 8, the configuration may include a shape having a series of proximal apices and a series of distal apices. A proximal end 362 of the stent 360 may comprise multiple adjacent proximal apices 362a and 362b, while a distal end 364 of the may comprise multiple adjacent distal apices 388 having bores 389 formed therein, as shown in FIG. 8. In FIG. 4, a first proximal apex 362a may comprise an end region 370 having a bore 371 formed therein. A second, adjacent proximal apex 362b may comprise an end region 375 having an integral barb 377 formed therein. Alternatively, both proximal apices 362a and 362b may comprise integral barbs 377.

The stent 360 may comprise multiple angled strut segments disposed between a proximal apex 362a or 362b, and a corresponding distal apex 364a. By way of example, first and second angled strut segments 367 and 368 may be provided. A first angled strut segments 367 may meet with an adjacent second angled strut segment 368, thereby forming a transition region 380. Expansion of the stent 360 is at least partly provided by the angled strut segments 367 and 368, which may be substantially parallel to one another in a compressed state, but may tend to bow outward away from one another in the expanded state shown in FIG. 8. Each transition region 380 may comprise a larger surface area relative to the angled segments, and at least one barb 382 may be disposed in at least one of the transition regions 380.

Each of the distal apices 388 of the stent 380 may be coupled to a proximal end 322 of the membrane 325, for example, using one or more sutures that are looped through the graft membrane 325 and the bores 389 of the stent 360. In this manner, the stent 360 may be used as an attachment stent for endovascular graft fixation. For example, the membrane 325 may overlap with an aneurysm to seal off fluid flow into the aneurysm, while the proximal end 362 of the stent 360 may extend in a proximal direction away from the graft material, e.g., to engage a healthy portion of a vessel wall away from a diseased portion of the aneurysm. As will be apparent, one or more additional stents may be coupled to an inner or outer surface of the membrane 325, i.e., at a location distal to the stent 360, to help maintain patency throughout the graft material.

In FIG. 8, a plurality of axial fibers 327 and circumferential fibers 328 are provided, either inside or outside of the membrane 325. The plurality of axial fibers 327 and circumferential fibers 328 may be provided in accordance with the plurality of axial fibers 27 and the plurality of circumferential fibers 28, as shown in FIGS. 1-2 above.

Further, in FIG. 8, a plurality of angled axial fiber bundles 327a-327d are shown positioned external to the membrane 325, though additional angled fiber bundles that are not depicted extend around the full circumference of the membrane 325. Each of the angled axial fiber bundles 327a-327d comprises multiple segments 391-394, though greater or fewer segments may be employed. Two individual fibers within each bundle 327a-327d may be looped through the bore 389 at a distal apex 388 of the stent 360, and therefore, the two individual fibers extend distally away from the stent 360 forming the four segments 391-394. The four segments 391-394 may fan outward relative to one another, i.e., become further spaced apart relative to each other as they extend in a proximal to distal direction, as shown in FIG. 8.

It is believed that by providing axial fiber bundles 327a-327d coupled to, and extending distally from, the stent 360 in the manner shown, wherein multiple segments 391-394 fan outward relative to one another, the fibers may be oriented in a manner that reinforces strength characteristics of stent-graft 320 while maintaining its lower profile. In particular, it is believed that such a structure of FIG. 8 may selectively reinforce the membrane 325 and allow the stent-graft 320 to withstand physiological fluid flow in a proximal to distal direction.

Figures 9A, 9B:
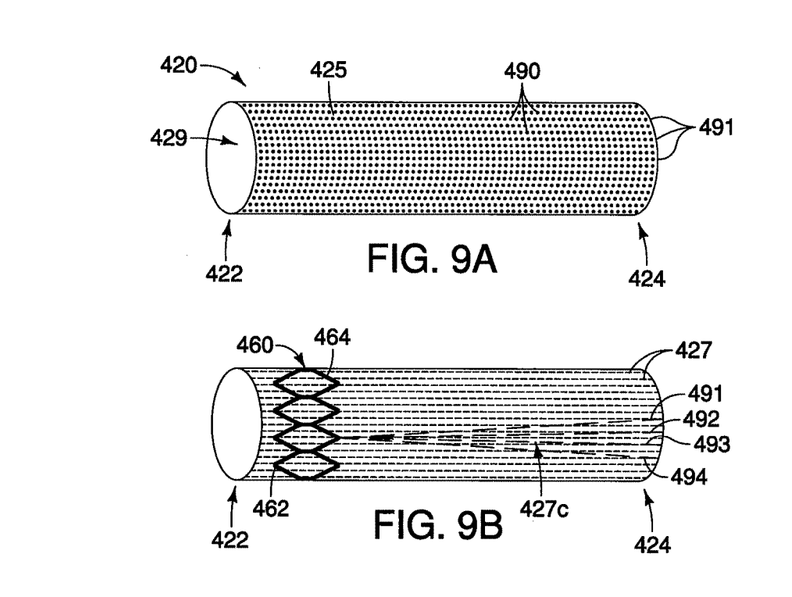
FIGS. 9A-9C illustrative exemplary methods steps for manufacturing a further alternative stent-graft.

Referring now to FIGS. 9A-9C, an alternative stent-graft 420 borrows various principles from the above-described stent-grafts, and comprises a membrane 425 having proximal and distal ends 422 and 424 and a lumen 429 extending therebetween. In one optional method step, depicted in FIG. 9A, multiple holes 490 may be drilled around the circumference of the membrane 425, thereby forming a plurality of rows 491. In one embodiment, about forty rows 491 may be formed. Then, a corresponding number of axial fibers 427 may be coupled to the membrane 425, as shown in FIG. 9B. For example, each axial fiber 427 may be looped through the holes 490 of a particular row 491. Alternatively, the holes 490 may be omitted and a desired number of axial fibers 427 may be arranged internal or external to or within the membrane 425.

Figure 9C:
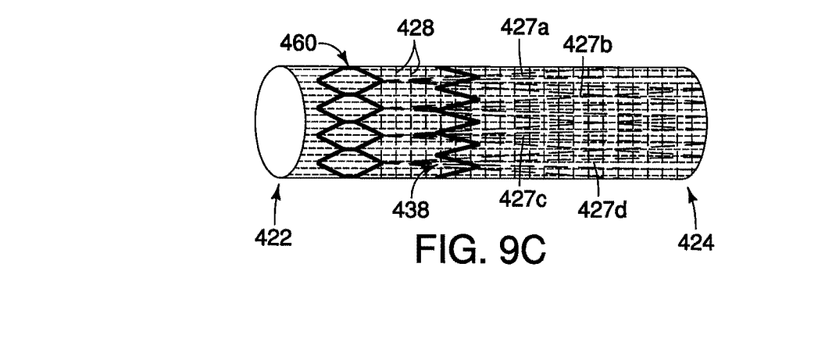

In FIG. 9B, after the axial fibers 427 have been coupled to the membrane 425, a proximal attachment stent 460 may be disposed external to the axial fibers 427. The stent 460 may be similar to the stent 360 described in FIG. 8, and may comprises a plurality of proximal and distal apices 462 and 464. A plurality of angled axial fiber bundles 427a-427d may be coupled to the stent 460 external to the membrane 425, as shown in FIGS. 9B-9C. Each of the angled axial fiber bundles 427a-427d comprises multiple segments 491-494, though greater or fewer segments may be employed. Two individual fibers within each bundle 427a-427d may be looped through bores at a distal apex 464 of the stent 460, in the manner shown in FIG. 8 above, and therefore the two individual fibers extend distally away from the stent 460 forming the four segments 491-494. The four segments 491-494 may fan outward relative to one another, i.e., become further spaced apart relative to each other as they extend in a proximal to distal direction, as shown in FIGS. 9B-9C.

As shown in FIG. 9C, in a next step, a plurality of circumferential fibers 428 then may be arranged outside of the membrane 425 and the angled axial fiber bundles 427a-427d at locations distal to the proximal stent 460. The plurality of circumferential fibers 428 may be provided in accordance with the plurality of circumferential fibers 28, as shown in FIGS. 1-2. In a final step, one or more stents 438, such as zig-zag shaped stents provided as described above, may be arranged over the plurality of circumferential fibers 428 at locations distal to the proximal stent 460, as shown in FIG. 9C. The stent 438 may be secured to the membrane 425. The stent-graft 420 then may be prepared by mounting the membrane 425 on a lathe. The lathe may be rotated at a proper speed, such as 20 rpm, while applying a dilute polyurethane solution to cover all of the fibers disposed distal to the proximal stent 460. The stent-graft 420 then may be cured at about 65 degrees Celsius for about 2 hours while the lathe is rotated at the desired speed.

Advantageously, like the stent-grafts above, it is believed that the stent-graft 420 of FIGS. 9A-9C may provide a selectively reinforced membrane 425 that may better withstand physiological fluid flow in a proximal to distal direction. Further, by selectively orienting axial fibers 427, angled axial fiber bundles 427a-427d, and circumferential fibers 428 at predetermined locations along the length and circumference of the stent-graft 420, but not continuously along the stent-graft 420, a significantly reduced delivery profile may be achieved.

Figure 10:
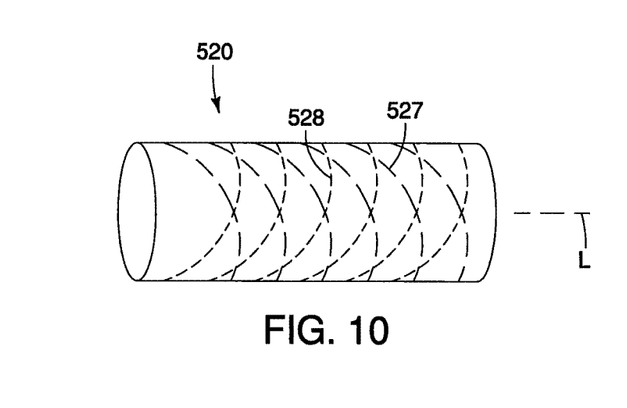
FIG. 10 is side view of a stent-graft according to a further alternative embodiment.

Referring to FIG. 10, in lieu of the generally axial and circumferential fibers 27 and 28 shown above, a further alternative stent-graft 520 may comprise a plurality of first fibers 527 and a plurality of second fibers 528, neither of which are substantially parallel or perpendicular to the longitudinal axis L of the prosthesis. The plurality of first fibers 527 and the plurality of second fibers 528 may be overlapping, but not interwoven. Such angled first and second fibers 527 and 528 may be more compliant than the axial and circumferential fibers 27 and 28 shown above, but still may be selectively arranged in a manner that may beneficially handle physiological loads, facilitate stent attachment to the membrane 525, and reduce the overall profile of the stent-graft 520, in the manner described above.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An endoluminal prosthesis, comprising:
   a membrane having a lumen for allowing fluid flow; and
   a plurality of circumferential fibers coupled to the membrane that form at least one bundled region in which at least two adjacent circumferential fibers are separated by a first spacing, and that form at least one-non-bundled region in which at least another two adjacent circumferential fibers are separated by a second spacing, where the first spacing is less than the second spacing, the second spacing is at least three times greater than the first spacing, and the circumferential fibers are not interwoven with any other fiber, and where each of the plurality of circumferential fibers extends around an entire circumference of the membrane.

2. The endoluminal prosthesis of claim 1 where at least one stent is coupled to the membrane using sutures only in at least one of the bundled regions.

3. The endoluminal prosthesis of claim 2 where the stent comprises a zig-zag shape having proximal and distal apices, where at least one of the proximal apices of the stent is secured to the membrane at a proximal bundled region, and where at least one of the distal apices of the stent is secured to the membrane at a distal bundled region, where the proximal and distal bundled regions are separated by at least one non-bundled region.

4. The endoluminal prosthesis of claim 1, further comprising a plurality of axial fibers extending in a direction that is generally parallel to a longitudinal axis of the endoluminal prosthesis.

5. The endoluminal prosthesis of claim 4, where the plurality of axial fibers overlap with at least one bundled region of circumferential fibers at intersections, and where at least one portion of a stent is secured to the membrane at one of the intersections.

6. An endoluminal prosthesis, comprising:
a membrane having a lumen for allowing fluid flow;
a plurality of axial fibers extending generally along a longitudinal axis of the endoluminal prosthesis, where each of the plurality of axial fibers are separated from one another by a spacing, and each of the plurality of axial fibers extends along the length of the membrane; and
a plurality of circumferential fibers disposed generally perpendicular to the plurality of axial fibers, where at least one circumferential fiber is separated from a first adjacent circumferential fiber by a first spacing, and where the at least one circumferential fiber is separated from a second adjacent circumferential fiber by a second spacing, where the second spacing is at least three times greater than the first spacing, and the circumferential fibers are not interwoven with any other fiber, and where each of the plurality of circumferential fibers extends around an entire circumference of the membrane.

7. The endoluminal prosthesis of claim 6 where at least one axial fiber is separated from a first adjacent axial fiber by a first spacing of axial fibers, and where the at least one axial fiber is separated from a second adjacent axial fiber by a second spacing of axial fibers, where the first spacing of axial fibers is less than the second spacing of axial fibers.

8. The endoluminal prosthesis of claim 7 where at least one stent is coupled to the membrane at an intersection where the at least one axial fiber and the first adjacent axial fiber meet at least one of the circumferential fibers.

9. An endoluminal prosthesis, comprising:
a membrane having a lumen for allowing fluid flow;
a plurality of circumferential fibers coupled to the membrane that form at least one bundled region in which at least two adjacent circumferential fibers are separated by a first spacing, and that form at least two non-bundled regions where in each of the non-bundled regions at least another two adjacent circumferential fibers are separated by a second spacing, where the first spacing is less than the second spacing;
at least one stent, where the at least one stent is sutured to the membrane only at the bundled regions; and
a plurality of axial fibers extending generally along a longitudinal axis of the endoluminal prosthesis, where at least one axial fiber is separated from a first adjacent axial fiber by a first spacing of adjacent axial fibers, and where at least one axial fiber is separated from a second adjacent axial fiber by a second spacing of adjacent axial fibers,
wherein the stent comprises a plurality of proximal and distal apices and wherein at least one of the proximal and distal apices of the stent is aligned with at least one axial fiber.

10. The endoluminal prosthesis of claim 9 wherein the second spacing is at least three times greater than the first spacing.

11. The endoluminal prosthesis of claim 9 where the at least one stent is coupled to the membrane at an intersection where at least one axial fiber meets at least one of the circumferential fibers.

12. The endoluminal prosthesis of claim 9 wherein the first spacing of adjacent axial fibers is substantially equal to the second spacing of adjacent axial fibers.

13. The endoluminal prosthesis of claim 9 wherein the first spacing of adjacent axial fibers is less than the second spacing of adjacent axial fibers.

14. The endoluminal prosthesis of claim 9 wherein the membrane has an interior surface and an exterior surface and wherein at least one axial fiber is disposed on the exterior surface of the membrane.

15. The endoluminal prosthesis of claim 14 wherein the at least one stent is disposed between the interior surface of the membrane and the at least one axial fiber.

16. The endoluminal prosthesis of claim 9 wherein a film is disposed over the at least one axial fiber thereby encapsulating the fiber between the membrane and the film.

17. The endoluminal prosthesis of claim 16 wherein the film comprises a polymeric material.

* * * * *